United States Patent
Vinokurov et al.

(10) Patent No.: US 9,337,603 B2
(45) Date of Patent: May 10, 2016

(54) ULTRA-SHORT TERAHERTZ PULSE GENERATOR HAVING MULTIPLE FOILS

(71) Applicant: KOREA ATOMIC ENERGY RESEARCH INSTITUTE, Daejeon (KR)

(72) Inventors: Nikolay Vinokurov, Novosibirsk (RU); Young Uk Jeong, Daejeon (KR)

(73) Assignee: KOREA ATOMIC ENERGY RESEARCH INSTITUTE, Daejeon (KR)

( * ) Notice: Subject to any disclaimer, the term of this patent is extended or adjusted under 35 U.S.C. 154(b) by 0 days.

(21) Appl. No.: 14/416,043

(22) PCT Filed: May 14, 2013

(86) PCT No.: PCT/KR2013/004244
§ 371 (c)(1),
(2) Date: Jan. 20, 2015

(87) PCT Pub. No.: WO2014/027737
PCT Pub. Date: Feb. 20, 2014

(65) Prior Publication Data
US 2015/0244135 A1    Aug. 27, 2015

(30) Foreign Application Priority Data
Aug. 16, 2012   (KR) ........................ 10-2012-0089647

(51) Int. Cl.
| | |
|---|---|
| *H01S 1/00* | (2006.01) |
| *H01J 25/00* | (2006.01) |
| *H01S 3/10* | (2006.01) |
| *G02B 6/04* | (2006.01) |
| *H01J 63/02* | (2006.01) |
| *G01N 21/3581* | (2014.01) |

(52) U.S. Cl.
CPC ................ *H01S 1/005* (2013.01); *H01J 25/00* (2013.01); *H01J 63/02* (2013.01); *G01N 21/3581* (2013.01)

(58) Field of Classification Search
CPC ............... H01S 1/00; H01S 1/02; H01S 3/10; H01S 3/30; G02B 6/04; G02B 27/44
USPC ........ 250/504 R, 338.1, 200, 493.1; 359/342, 359/566, 575; 372/102, 20, 21, 37, 4, 372/43.01, 92, 98; 378/98, 119, 125
See application file for complete search history.

(56) References Cited

U.S. PATENT DOCUMENTS

| | | | |
|---|---|---|---|
| 7,272,158 B1 * | 9/2007 | Hayes ..................... | G02F 1/365 372/21 |
| 8,467,430 B2 * | 6/2013 | Caffey ................... | B82Y 20/00 372/102 |
| 8,947,769 B1 * | 2/2015 | Korenblit .................. | H01S 1/02 359/342 |

(Continued)

FOREIGN PATENT DOCUMENTS

| | | |
|---|---|---|
| JP | 2003-500862 | 1/2003 |
| JP | 4759770 | 6/2011 |

(Continued)

OTHER PUBLICATIONS

International Search Report and Written Opinion for PCT/KR2013/004244, mailed Jul. 11, 2013, 9 pages.

*Primary Examiner* — David A Vanore
(74) *Attorney, Agent, or Firm* — Morrison & Foerster LLP

(57) ABSTRACT

This specification relates to a terahertz pulse generator capable of generating ultra-short terahertz pulses by use of electron beams transported through a plurality of foils. The plurality of foils in a shape of disc are arranged in an overlapped state and form a conical shape that diameters of the disc-shaped foils sequentially decrease along a direction that the electron beam is transported. Coherent radiation, which is generated as the ultra-short electron beam is transported through the foils in respective spaced gaps of the foils, is propagated toward the outside of the disc-shaped foils and gathered with forming a conical wave surface at edges of the disc-shaped foils. This may result in enhancement of generation efficiency of the terahertz waves.

9 Claims, 3 Drawing Sheets

(56) References Cited

U.S. PATENT DOCUMENTS

| | | | | |
|---|---|---|---|---|
| 2005/0018298 A1* | 1/2005 | Trotz | ................... | G01N 21/35 359/575 |
| 2010/0072405 A1* | 3/2010 | Yu | ........................ | H01J 25/02 250/493.1 |
| 2010/0276612 A1* | 11/2010 | Norwood | ................ | G01J 3/108 250/504 R |
| 2014/0166881 A1* | 6/2014 | Han | ................... | G01N 21/3581 250/338.1 |
| 2015/0061784 A1* | 3/2015 | Hong | ...................... | H01J 23/24 331/82 |
| 2015/0090906 A1* | 4/2015 | Kim | ....................... | G02F 1/353 250/504 R |

FOREIGN PATENT DOCUMENTS

| | | |
|---|---|---|
| JP | 2012-23134 | 2/2012 |
| KR | 10-2011-0082419 | 7/2011 |

\* cited by examiner

ULTRA-SHORT TERAHERTZ PULSE GENERATOR HAVING MULTIPLE FOILS

CROSS-REFERENCE TO RELATED APPLICATIONS

This application is the national phase of PCT application PCT/KR2013/004244 having an international filing date of 14 May 2013, which claims benefit of Korean patent application No. 10-2012-0089647 filed 16 Aug. 2012. The contents of the above patent applications are incorporated by reference herein in their entirety.

TECHNICAL FIELD

The present disclosure relates to a method and apparatus for generating high-power ultra-short terahertz pulses by high-energy ultra-short electron bunches passing through a set of thin foils.

BACKGROUND ART

Terahertz waves occupy the middle ground between infrared light waves and microwaves and consist of electromagnetic waves at frequencies approximately between 0.1 and 10 terahertz (THz). The terahertz waves have frequencies corresponding to an intermediate range between radio waves and light waves. The terahertz waves are also called submillimeter waves or far infrared waves.

Frequencies of the terahertz waves correspond to molecular vibration frequencies of large molecules. Especially, the terahertz waves may be very useful for analysis of biological materials with very long molecules. Also, it is advantageous that the terahertz waves are used for analyzing fine properties which are unable to be directly measured using other techniques. Development and researches for various technologies using the terahertz waves are actively in progress in various fields such as security inspection, diagnosis, material analysis, next generation communication and the like.

The main factor that the development of the terahertz technology is more delayed than other electromagnetic wave bands, such as visible rays, infrared rays or microwaves, is the difficulty in generating and detecting terahertz radiation. In recent time, techniques of generating ultra-short terahertz waves using ultra-short laser or electron beam pulses having a time width of picoseconds ($10^{-12}$ sec) or less are actively being developed. However, the terahertz frequency range still exhibits extremely low generation efficiency as compared with other neighboring electromagnetic wave ranges. This may cause lasers or accelerators to become very large in size in order to obtain high-power terahertz waves. Such high-power terahertz waves are also generated using large accelerators. In order to generate the high-power ultra-short terahertz waves using small-scale accelerators, instead of large accelerators which are high-priced, it is necessary to develop a new technique of generating terahertz waves with improved efficiency. This is one of the most important tasks in the terahertz science and technology field worldwide.

Transition radiation is radiation emitted when a relativistic electron passes through a boundary between two media having different refractive indexes from each other. In general, a thin conducting foil is widely used as the boundary. Incoherent transition radiation shows quite low efficiency of converting kinetic energy of an electron into radiation. When the transition radiation meets a coherent condition, output and generation efficiency may also increase. When a length of an electron beam used for radiation generation becomes shorter than a characteristic wavelength of radiation generated, the output and the generation efficiency may be enhanced by virtue of a coherent effect. Upon use of ultra-short electron beam pulses below picoseconds, the coherent transition radiation may be generated at the terahertz frequency range, and in this case, approximately $10^{-5}$ to $10^{-4}$ of the electron beam kinetic energy may be converted into the radiation.

High-energy ultra-short terahertz waves reaching up to 100 MW have recently been generated by a large accelerator according to the aforementioned method. Even in this case, the generation efficiency of the terahertz waves is still rather low.

DISCLOSURE OF INVENTION

Technical Problem

In order to generate terahertz waves by using the coherent transition radiation method with ultra-short electron beams, a sheet of conducting foil has been used in the related art. For increasing the energy of the ultra-short terahertz pulse, the number of electrons of an electron bunch incident onto the one sheet of foil has to increase. To increase the number of particles, not only technical and physical limitations, such as an excessive space charge repulsion due to many electrons accumulated within a small volume, but also economic issues of increasing scale and capacity of an accelerator have to be overcome.

Solution to Problem

To achieve these and other advantages in accordance with the purpose of the present invention, as embodied and broadly described herein, there is provided an ultra-short terahertz pulse generator, including a plurality of foils arranged in one direction and forming spaced gaps by being spaced apart from one another, the plurality of foils being arranged such that at least partial area is overlapped, and an accelerator configured to generate electron beams going along the one direction to pass through the foils such that ultra-short terahertz waves are generated inside the gaps between the foils.

In accordance with one aspect of the present disclosure, each foil may be formed in a shape of disc, and diameters of the foils may decrease successively along the direction, normal to the foil surface.

In accordance with one aspect of the present disclosure, the foils may be arranged such that centers thereof come into alignment, and the electron beam may be transported through the centers.

In accordance with one aspect of the present disclosure, diameters of the foils may linearly decrease, and a conical shape may be formed when edges of the foils are connected.

In accordance with one aspect of the present disclosure, the foil may be formed of a conducting material, and the ultra-short terahertz pulses may be generated by the electron beam in the spaced gaps so as to be propagated in a direction perpendicular to the beam direction.

In accordance with one aspect of the present disclosure, the ultra-short terahertz pulses which are generated and propagated inside the spaced gaps may be gathered into one wave surface at edges of the spaced gaps, so as to be radiated into a free space.

In accordance with one aspect of the present disclosure, the foils may be arranged in parallel to one another such that the spaced gaps are uniformly defined.

In accordance with one aspect of the present disclosure, the electron beam may be transported along a direction perpendicular to the foils.

In accordance with one aspect of the present disclosure, the spaced gap may be maintained in a vacuum state or filled with a dielectric substance.

Advantageous Effects of Invention

In accordance with the detailed description, as ultra-short high-energy electron bunches are transported through a plurality of foils, coherent transition radiation of the terahertz frequency range waves, generated in each spaced gap between the foils, may be radiated as one wave. This may result in enhancement of generation efficiency of terahertz waves.

MODE FOR THE INVENTION

Hereinafter, description will be given of an ultra-short terahertz pulse generator in accordance with exemplary embodiments of the present disclosure with reference to the accompanying drawings. Incidentally, unless clearly used otherwise, expressions in the singular number include a plural meaning.

Also, in this application, the terms "comprising" and "including" should not be construed to necessarily include all of the elements or steps disclosed herein, and should be construed not to include some of the elements or steps thereof, or should be construed to further include additional elements or steps.

Figure 1:
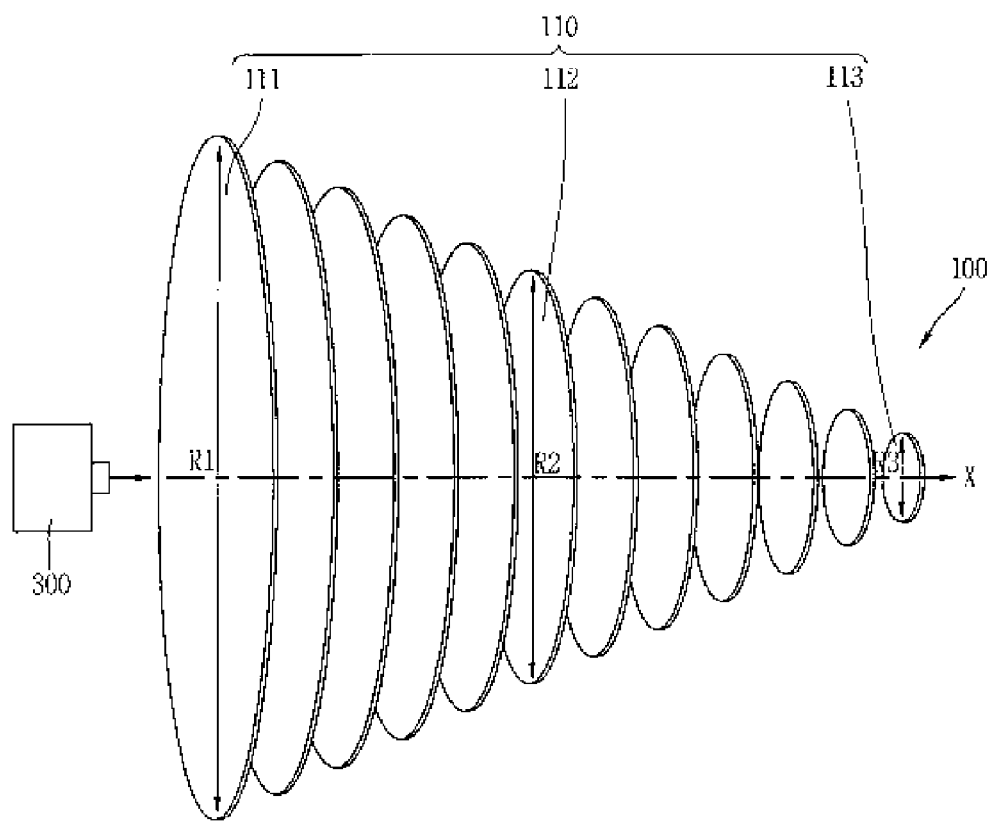
FIG. 1 is an overview showing an ultra-short terahertz pulse generator.
Figure 2A:
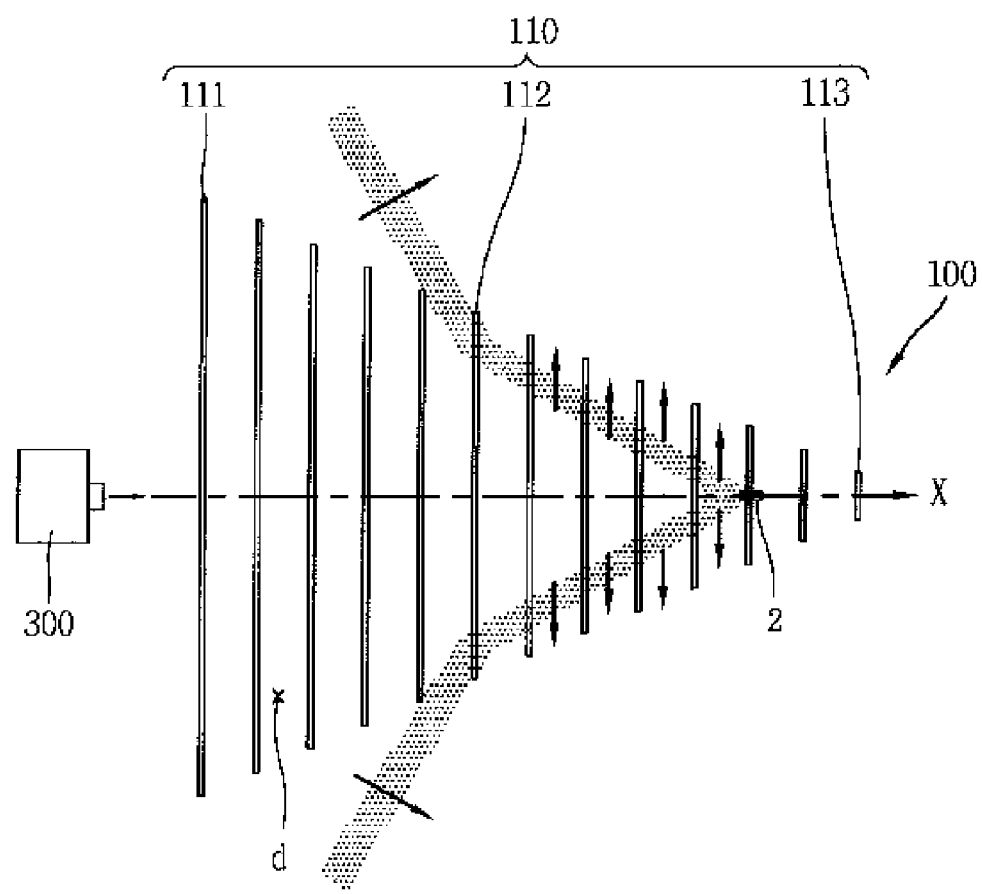
FIGS. 2A and 2B are front views of the ultra-short terahertz pulse generator of FIG. 1 to illustrate generation of ultra-short terahertz pulse.
Figure 2B:
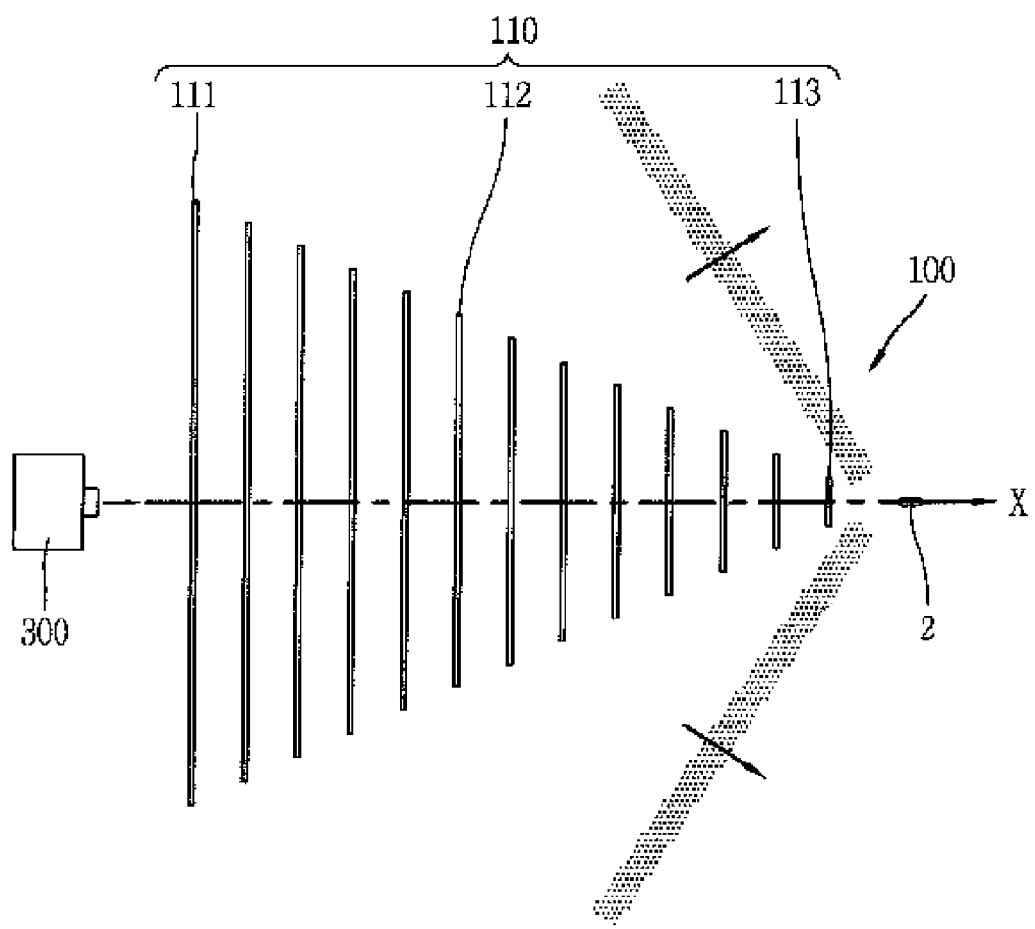

FIG. 1 is an overview showing an ultra-short terahertz pulse generator, and FIGS. 2A and 2B are front views of the ultra-short terahertz pulse generator of FIG. 1 to illustrate generation of ultra-short terahertz wave.

As shown in FIGS. 1 and 2, an ultra-short terahertz generator 100 according to an exemplary embodiment may include a plurality of foils 110. An ultra-short high-energy electron bunch 2 emitted from an electron accelerator 300 may go along an X-axial direction and pass through the foils 110.

The electron accelerator 300 is an apparatus for generating electrons having high kinetic energy by accelerating the using an electrostatic field, a high-frequency electric field within an accelerating cavity or the like. The electron accelerator 300 according to the present disclosure is designed to emit ultra-short electron bunches in the X-axial direction that the ultra-short terahertz wave generator 100 is disposed.

The electron beam has to consist of relativistic electrons whose kinetic energy is over about million electron volts (MeV), and preferably of an ultra-short electron bunches whose duration is less than picoseconds (10-12 sec) in order to generate coherent transition radiation at a frequency range of terahertz waves by transporting the electron beam through the ultra-short terahertz generator 100.

Each foil of the set 110 has a shape of a thin plate with a thickness less than several tens of micrometers. The foils 110 may preferably be formed of, but not limited to, a metal so as to reduce a propagation loss of transition radiation generated. That is, the foil 110 may be formed of other materials. The foil 110 may preferably be formed as thin as being capable of ignoring deformation of a pulse width due to energy loss of the electron beam 2 passing through the plurality of foils 110 and multiple scattering. FIGS. 1 and 2 exemplarily show 12 foils but the present disclosure may not be limited to the number of foils.

The plurality of foils 110 may be formed in a disk shape. Those foils 110 may be arranged with being spaced apart from one another by gaps d. The gap d formed between the spaced foils 110 may be formed uniformly or differently. The spaced gap d may be formed in a vacuum state or filled with a dielectric substance.

The plurality of foils 110 may be arranged such that a width of the spaced gap d can have a smaller value than a characteristic wavelength of terahertz wave generated. While the electron bunch 2 moves through the plurality of foils 110 arranged, coherent transition radiation is emitted.

The radiation field propagates in a form of transverse electromagnetic (TEM) wave toward the outside of the disk between the metal foils. The electromagnetic wave propagating in the form of TEM wave may not be spread, accordingly, an ultra-short pulse may be retained. The TEM wave may be characterized by the fact that an electric vector and a magnetic vector which are perpendicular to each other are perpendicular to a direction of propagation.

The radiation may be propagated away from the inside of the spaced gap d toward the outside of the disks. Then, the radiation of different gaps is combined, forming a conical-like wave in a free space. Thus, the radiator emits the coherent wave. Therefore, the terahertz wave radiated into a space may be gathered by using a separate focusing optical system (not shown).

In the meantime, in order to have a coherent radiated wave, preferably, the plurality of foils 110 may substantially be disposed in parallel to one another.

The terahertz wave generator according to the present disclosure may include the plurality of foils 110. Terahertz waves may be generated from each of the plurality of foils 110 by the ultra-short electron beam 2, and those terahertz waves may be combined and form one wave surface. This may result in enhancing generation efficiency of the transition radiation. Also, an increase ratio of output or generation efficiency of the radiation may be in proportion to the number of foils 110 provided in the terahertz wave generator.

The foil disks 110 may be arranged such that their centers can lay on the same straight line. Then the electron beam 2 may be transported through the centers.

Also, the disk-shaped foils 110 may have different diameters from one another. The dependence of the foil diameter on its number may be adjusted to obtain the desirable shape of the wave front of the radiated wave. In particular, the difference of the diameters between the neighbor foils may be the same. That is, the foils 110 may be formed such that their diameters can change linearly.

The centers of the foils 110 may lay on the same straight line (X-axis), normal to the foil surfaces, and the diameters of the foils 110 may linearly decrease along the X-axial direction. Accordingly, when edges of the foils 110 are connected, they may form a part of a conical shape.

Also, the foils of plurality may have a shape, different from disks, like ellipses, rectangles, or others. Then the radiated wave front is not axisymmetric.

The ultra-short electron bunch may be transmitted through the metallic foils. The coherent radiation of the terahertz frequency range, radiated into the spaced gap, may be propagated in a radial direction which is perpendicular to the X-axial direction by a parallel-plate waveguide which is defined by the foils. The propagated terahertz wave is in a TEM mode, which has no dispersion (phase velocity does not depend on frequency). Therefore, the ultra-short terahertz pulse may be retained.

The ultra-short terahertz pulses propagated in the radial direction inside spaced gaps may be combined in a free space, with forming one conical wave surface at the edges of the foils.

The wave surface may be conically formed and a radiation central axis of the radiation may be the X-axial direction (x). Hence, radiation generated in each spaced gap between the plurality of foils 110 may be gathered into a wave having one wave surface in one space. This may allow for providing ultra-short terahertz wave having greater energy.

Referring to FIG. 2, the ultra-short electron bunch 2 may be transported through the centers of the respective foils 110 overlapped by one another. While the electron bunch 2 is transported through the foils 110, the radiation may move from the centers of the foils 110 toward their edges.

The radiation may be generated inside the spaced gaps d and propagated in the radial direction. A diameter of the disk-shaped foil 110 may decrease along the X-axial direction.

The radiation may be propagated in the form of TEM wave. Hence, the electromagnetic wave may not spread, and this may allow for maintaining an ultra-short pulse. Therefore, since the radiation generated in the spaced gap between the plurality of foils 110 is gathered with forming one wave surface, it may be possible to generate the stronger ultra-short terahertz pulse.

Therefore, it may be advantageous in that the generation efficiency of the ultra-short terahertz waves by the same accelerator performance can be enhanced and a cost required to enhance the performance of an electron accelerator may be reduced.

In the meantime, a diameter difference of the disk-shaped foils 110 may be set to increase or decrease in a non-linear manner. That is, the wave surface of terahertz wave radiated may be adjusted by varying the diameter difference.

The aforementioned ultra-short terahertz wave generator may not be construed to be limited by the configuration and method of the foregoing embodiments, but rather a part or all of the embodiments may be selectively combined to obtain additional and/or alternative exemplary embodiments.

The invention claimed is:

1. An ultra-short terahertz pulse generator comprising:
a plurality of foils arranged in one direction, the plurality of foils being arranged such that at least parts of their areas are overlapped;
wherein spaced gaps are formed between the at least parts of the areas of the plurality of foils that are overlapped, and
an accelerator configured to generate short electron bunches going along one direction normal to the foil surfaces to pass through the plurality of foils,
whereby when the short electron bunches pass through the plurality of foils and the spaced gaps ultra-short terahertz pulses are generated inside the gaps between the foils.

2. The generator of claim 1, wherein each foil is formed in a shape of disc, and
wherein diameters of the foils decrease along the one direction.

3. The generator of claim 2, wherein the foils are arranged such that centers thereof come into alignment, and
wherein the electron beam passes through the centers.

4. The generator of claim 3, wherein diameters of the foils linearly decrease, and a conical shape is formed when edges of the foils are connected.

5. The generator of claim 4, wherein the foils are formed of a conducting material, and
wherein the ultra-short terahertz pulses are propagated in a direction perpendicular to the one direction as the electron beam is propagated in each of the spaced gaps.

6. The generator of claim 5, wherein the wave surfaces of the ultra-short terahertz pulses emitted are gathered into a conical shape at edges of the spaced gaps, such that the ultra-short terahertz waves are radiated with maintaining a wave surface of the conical shape.

7. The generator of claim 5, wherein the foils are arranged in parallel to one another such that the spaced gaps are uniformly defined.

8. The generator of claim 7, wherein the electron beam is transported along a direction perpendicular to the foils.

9. The generator of claim 1, wherein the spaced gaps are maintained in a vacuum state or filled with a dielectric substance.

* * * * *